United States Patent [19]

Ruddock

[11] 4,314,986

[45] Feb. 9, 1982

[54] METHOD AND CONTAINER FOR REDUCING PERTECHNETATE

[75] Inventor: Clinton F. Ruddock, Amersham, England

[73] Assignee: The Radiochemical Centre Limited, England

[21] Appl. No.: 124,237

[22] Filed: Feb. 25, 1980

[30] Foreign Application Priority Data

Feb. 27, 1979 [GB] United Kingdom .............. 06883/79

[51] Int. Cl.$^3$ ...................... A61K 49/00; A61K 43/00
[52] U.S. Cl. .......................................... 424/1; 422/61; 423/249; 424/9
[58] Field of Search ...................... 424/1, 9; 206/569; 422/61; 423/249

[56] References Cited

U.S. PATENT DOCUMENTS 3,873,680   3/1975   Jackson et al. ......................... 424/1
3,902,849   9/1975   Barak et al. ................. 252/301.1 R

OTHER PUBLICATIONS

Persson et al., Int. J. App. Rad. Isot., vol. 28, 1977, pp. 97–104.

Primary Examiner—Christine M. Nucker
Attorney, Agent, or Firm—Wenderoth, Lind & Ponack

[57] ABSTRACT

A method of reducing the pertechnetate in $TcO_4^-$ comprises mixing together an aqueous solution of pertechnetate, e.g. the eluent from a technetium generator, metallic tin or an alloy thereof as a reducing agent for the pertechnetate, and a soluble salt of a metal below tin in the electrochemical series, e.g. copper, as an activator for the tin metal reducing agent. A complexing agent for the reduced technetium or a colloid stabilizer may also be included. The pH is preferably 3 to 12. Also claimed is a closed container containing the tin reducing agent, the activator, and the complexant or colloid stabilizer if used, preferably in a freeze-dried sterile state, to which the pertechnetate solution may be added.

8 Claims, No Drawings

METHOD AND CONTAINER FOR REDUCING PERTECHNETATE

This invention relates to a method for reducing pertechnetate. The technetium-99m isotope is conveniently available in solution in the form of the chemically stable pertechnetate ion ($TcO_4^-$). Aqueous solutions of pertechnetate ion are eluted, frequently by a saline eluent, from generators containing the long-lived parent molybdenum-99. Pertechnetate itself has only limited applications in diagnostic scanning because it does not readily form complexes with materials which locate in specific parts of the body. It has therefore long been general practice to reduce technetium from the 7-valency in pertechnetate to the 3-, 4- or 5-valency in which it readily forms complexes with a wide variety of materials. Many reducing agents have been tried over the last twenty years for this purpose, but the current reducing agents of choice are stannous salts (e.g. chloride, fluoride or tartrate). Despite widespread commercial utilisation, stannous reducing agents suffer from a number of serious disadvantages:

(i) Stannous salts are unstable during production, storage and after labelling, both with respect to hydrolysis in solution and to oxidation. This leads to losses caused by oxidation and to labelled impurities as a result of hydrolysis.

(ii) Stringent precautions need to be taken by the manufacturer to minimise oxidation, including nitrogen purging of all solutions used in preparation and of vials sent out to customers.

(iii) To compensate for expected losses of stannous ions, manufacturers tend to use a very large stoichiometric excess. The use of a large excess is undesirable because of possible toxicity.

(iv) Without these precautions, the shelf life of vials containing stannous salts as reducing agents is generally poor, and even with them is occasionally less than is desired.

Our co-pending published British patent application No. 2016198 filed Mar. 1, 1979 describes a method of reducing pertechnetate using tin or a tin-containing alloy as a reducing agent in the presence of a complexant for the reduced technetium. For reasons described therein, this method is greatly superior to the use of a stannous salt reducing agent, but it does itself have some disadvantages:

(a) Tin metal and its alloys, as supplied by the manufacturers and subjected only to a simple de-greasing treatment, are not entirely reliable as reducing agents, in that, although they normally function perfectly effectively to reduce the pertechnetate within a few minutes, an occasional batch of material or, more particularly, part of a batch of material, fails to act as an effective reducing agent. It is believed that the reduction may take place on the surface of the metal rather than in the liquid medium and may therefore be inhibited by an oxide film. Although this disadvantage may be overcome by strict selection and quality control of the tin or its alloy, this increases costs, and may not be wholly effective for weakly complexing ligands.

(b) It is possible to improve the reliability of tin and its alloys be activating them, for example, by immersion in concentrated hydrochloric acid for one minute followed by washing in ethanol. This treatment certainly improves the reliability of the metal when it is used soon after treatment. However, for commercial operation, the treated material may need to be stored in its finally dispensed form for many months, and the reliability deteriorates under these circumstances.

(c) Tin metal and its alloys are only effective as reducing agents for pertechnetate in the presence of a complexant for the reduced technetium. The method does not work significantly in the absence of a complexant, and cannot therefore be used to make, for example, aqueous dispersions of technetium dioxide $TcO_2$, unless the tin is etched in acid immediately prior to use.

It is an object of the present invention to overcome these disadvantages.

The present invention provides a method of reducing pertechnetate $TcO_4^-$, which method comprises mixing together an aqueous solution of pertechnetate, metallic tin or an alloy thereof, and a soluble salt of a metal below tin in the electrochemical series.

Metals below tin in the electrochemical series include copper, silver, gold, mercury, arsenic, antimony, bismuth, platinum and the platinum metals. In principle, a salt of any of these may be used which is soluble in the aqueous solution of pertechnetate. In practice, there are limitations of choice, in that:

(a) many are toxic and, even though they might be used in amounts so small that no toxic effects would be observed, there is a natural reluctance to use them;

(b) silver salts cannot be used in presence of chloride ion, and chloride ion is normally present in the pertechnetate solution;

(c) some of the metals form strong complexes with certain of the complexing ligands employed for the technetium, or may otherwise interact with these ligands.

Our preferred noble metal is copper. Any physiologically acceptable cupric salt may be used, such as for example the sulphate or the chloride.

The amounts of metal salt required to activate the tin reducing agent are very small. As little as 1 microgram (expressed as weight of metal ion) can be effective, though it is preferred to use 10 to 1,000 micrograms in order to be sure of effecting reduction of the pertechnetate in a conveniently short time. There is no critical upper limit on the amount of metal salt which will work as an activator. A practical upper limit is set by the metal salt concentration that is acceptable for injection into patients for diagnostic scanning.

The solution of pertechnetate is conveniently the sterile eluate from a technetium generator, e.g. an aqueous solution of pertechnetate normally in isotonic saline. The precise nature of the solution is not critical, and generally no pre-treatment of the solution is required.

Commercial or analytical grade tin, or even 99.999% purity tin, may be used in the method with success. Alloys of tin with other metals are reliable and effective reducing agents. Since the amount of pertechnetate to be reduced is very small, the proportion of tin in the alloy determines to some extent the rate of reduction but is not otherwise critical and alloys containing as little as 5% tin are useful. Alloys of tin with gold, mercury, silver and lead, (e.g. solder) are suitable, and among these alloys of 0.5% to 10% by weight silver, balance tin, are particularly satisfactory and reliable. Alloys may have advantages over tin, other than improved reactivity and reliability, for example better mechanical strength, malleability and resistance to corrosion.

The reduction of technetium by means of the noble metal activated tin reducing agent occurs equally well in the presence or absence of a complexant.

When the mixture contains a complexant for technetium, the technetium, upon reduction from the 7+ valency state to a lower valency state, becomes attached to the complexant. In general, the nature of the attachment is not precisely known, though it is believed that electron donation from the complexant (donor ligand) to the technetium (acceptor ion) is involved. In many cases there is chromatographic evidence for more than one Tc-complex species. The compounds which may be labelled with technetium-99m in this way are herein called complexants. A large number of them suitable for use in this invention are available for diagnostic scanning of different parts of the body, as the following non-exhaustive list indicates:

1. Brain scanning—Diethylenetriamine penta acetate (DTPA), gluconate, glucoheptonate.
2. Kidney scanning—DTPA, gluconate, glucoheptonate, dimercaptosuccinate (DMSA), citrate.
3. Bone scanning—Methylenediphosphonate (MDP), pyrophosphate.
4. Myocardial infarct scanning—MDP, pyrophosphate.
5. Hepatobiliary scanning—N-2, 6-(dimethyl phenyl) carbamoylmethyliminodiacetic acid (HIDA), diethyl HIDA.
6. Deep vein thrombus detection (DVT)-Fibrinogen, streptokinase, urokinase.
7. Blood pool visualisation—human serum albumin.
8. Lung—macroaggregated albumin, albumin microspheres.
9. Liver—stabilised colloids, e.g. colloidal sulphur stabilised by gelatin, polyvinyl pyrrolidone, dextran.
10. Other—amino acids, thioglucose, thiomalate.

If a complexant is not used, the pertechnetate appears to be reduced to technetium dioxide, $TcO_2$, the aqueous dispersion of which may be stabilised by means of a colloid stabiliser such as, for example, gelatin, polyvinyl pyrrolidone, carboxymethyl cellulose or dextran. A colloid stabiliser is not necessary to achieve reduction of the pertechnetate, but may assist in preventing aggregation of the particles of the reduced technetium.

Since the amount of pertechnetate introduced into the mixture is very small, the amount of complexant or colloid stabiliser and metallic reducing agent present will necessarily be greatly in excess of the stoichiometric and are not critical. Amounts of from 1 mg. to 1 g. of complexant or colloid stabiliser are likely to be satisfactory for handling the product of one elution, e.g. from 0.5 to 50 ml. and typically 1 to 15 ml., of a commercial technetium generator. The surface area of the metallic reducing agent present determines the rate of reduction of the pertechnetate; enough tin should be used to ensure reduction in a conveniently short time. From 0.1 to 10 $cm^2$ is generally sufficient; for example, we have found that a piece of analytical reagent grade granular tin (99.9%) weighing 100–200 mg., or a piece of analytical grade tin foil measuring 0.5 cm.×1 cm.×0.25 mm., is sufficient to effect complete reduction of 100 mCi of pertechnetate in 5–10 minutes.

One of the advantages of using metallic tin, rather than a stannous salt, as a reducing agent for the pertechnetate is that the resulting solution does not contain any significant quantity of stannous ions. With this in mind, the pH of the mixture formed according to the present invention is preferably in the range 3 to 12, since outside this range tin is to some extent soluble in aqueous media. The nature of the noble metal salt may impose some further limitation; for example, copper salts are in general not soluble in aqueous media under alkaline conditions. The pH of the mixture can be adjusted, e.g. by means of a solid buffer or by the addition of acid or alkali to the pertechnetate solution to a value which is optimum for the complexant being used.

For the preparation of diagnostic scanning agents, reagent mixtures are frequently supplied in bottles each closed by a pierceable autoclavable closure and containing individual doses of reagents in a dry state intended to be activated by aseptic injection of the pertechnetate solution eluted from a generator. According to the present invention, the metal salt and optionally the complexant for technetium or the colloid stabiliser may be metered into each individual bottle, either as a solution or dispersion followed by freeze drying, or by dry dispensing, e.g. as a powder or tablet. The metal may be present in a convenient form such as foil, granules, wire or shot, and may be loose in the vessel. The use of loose metal powder is not recommended because of the risk that the powder may be drawn up by the hypodermic syringe used to extract the diagnostic scanning solution from the vessel. Alternatively the metal may be provided as a coating, e.g. by coating on the internal walls of the vessel or on an inert support; for example, inert plastics spheres, suitably 0.3 to 1.0 cm. diameter, may first be rendered electrically conducting, e.g. by vacuum evaporation of gold, and then electroplated with tin. Alternatively again, the metal may be carried by or associated with the pierceable autoclavable closure, in which case inversion of the vessel would be necessary to form the mixture and effect reduction of the pertechnetate.

Our preferred arrangement is to fix the tin or tin alloy to a piece of flexible chemically inert foil, e.g. of stainless steel or a plastics material such as cellulose acetate, and to position the foil in curved configuration round the inside wall of the bottle. For example a piece of tin foil may be stuck to the flexible foil with adhesive, or tin metal may be electroplated on to the foil if necessary via an intermediate metal. The foil itself should be sufficiently elastic to be held in curved configuration by friction round the wall of the bottle. Positioning the tin in the bottle in this way has advantages. First, it may be positioned near the bottom of the bottle so as to be immersed in the pertechnetate solution when the bottle is upright; or it may be positioned near the neck of the bottle so as to be immersed in the pertechnetate solution only while the bottle is tilted; this may be useful if it is desired to dispense the metal salt as a liquid and lyophilise it in the bottle without permitting it to contact the tin, or if it is desired to contact the pertechnetate solution with the tin only for a limited period of time. Second, it is out of the way so there is no danger that a technician who uses a hypodermic syringe to withdraw liquid will stick the needle into metal or plastics material.

The tin or tin alloy should be degreased to render it wettable. It may also be activated by removal of the oxide layer, for example by immersing in concentrated hydrochloric acid followed by washing in ethanol.

Good results can be achieved without activation however.

Providing the contents of the container in the solid state gives rise to an improvement in reliability and possibly also shelf life. Even if the metal salt is in physical contact with the tin reducing agent, solid state chemical reactions and corrosion or oxidation of the metal are unlikely to take place to any significant extent. However, if the solid mixture is prepared by freeze drying a solution in the container, the tin metal should preferably either be out of contact during the freeze drying, or added after completion of the freeze drying.

Other materials may be included in the container. A buffer may be provided to control the pH of the liquid mixture formed by addition of the pertechnetate solution at a desired value in the range 3 to 12; suitable buffers are physiologically acceptable materials known in the art such as phosphate, TRIS-buffer, bicarbonate, acetate. Preservatives and antioxidants may be used. The closed container may contain nitrogen or some other inert gas in place of air. When the technetium complex is lipophilic, it may be useful to add a water-miscible organic solvent such as ethanol; however, this should be added together with, or just before, the pertechnetate solution.

Only a single piece of metal need be used; of course, more than one piece may be used, but no advantage in performance is gained, whether or not the pieces are maintained in electrical contact. It is preferred to use a fresh piece of metal for each reduction; if one piece of metal is used repeatedly surface deactivation may become a problem.

The present invention has the following advantages over the conventional reduction method using stannous salts:
(i) Problems of stannous salt instability during production, storage and after labelling are eliminated—reducing both losses by oxidation and labelled impurities due to hydrolysis.
(ii) Production procedures are simplified e.g. by the use of cut metal foil or coated vials and powder dispensed ingredients.
(iii) It is no longer necessary, though it may still be advantageous, to nitrogen purge vials before sterilisation.
(iv) It reduces toxicity, because the only tin solubilised is the minute amount oxidized in reducing the pertechnetate. Since it is not necessary to have a large excess of stannous salt present in the solution to compensate for losses, it is not necessary to provide additional amounts of complexant to complex the stannous salt, and it is therefore possible to use smaller quantities of all ingredients.
(v) The shelf life of diagnostic scanning kits may be improved.
(vi) The metal reducing agent may be subjected to sterilisation by $\gamma$-irradiation without deteriorating, unlike certain stannous salts.
(vii) The labelling technique can be performed over a wide pH range, and particularly in alkaline solution thus giving rise to the possibility of labelling new molecules.
(viii) Virtually no stannous ion is present in vivo such as might interfere with a subsequent test.

While the invention is of value as a quick, reliable and simple route to all technetium complexes that are used for diagnostic scanning, it is of particular advantage in the following areas:

(a) Where the tin compound with the complexing agent is insoluble in water, for example aluminon. In such cases, stannous salts could not readily be used as reductants.
(b) Where the reaction between the reduced technetium and the complexant is slow in comparison with the rate of hydrolysis and/or oxidation of an alternative stannous salt reducing agent, for example saccharic acid and sugars generally. In such cases, the use of stannous salts as reducing agents tends to result in the formation of a colloidal dispersion of unreactive technetium dioxide.
(c) Where the complexant ligand is weak and liable to hydrolyse in the absence of an excess of the complexant, e.g. gluconate.

The following Examples illustrate the invention. Except where stated, the metallic reducing agent was a 5×10 mm. piece of tin foil 0.1 mm. thick of 99.5% purity supplied by British Drug Houses, which was degreased but not activated before use. These laboratory experiments were not performed under sterile conditions, and in some cases pH adjustment was effected immediately after addition of the pertechnetate solution. For commercial operation, however, the buffer would normally be pre-dispensed in dry form along with the complexant and the metallic reducing agent. In all cases, the pertechnetate solution was the isotonic saline eluate from a technetium-99m generator. Measurement of the extent of complex formation was by thin layer chromatography on silica gel, by means of elution, first with methylethyl ketone and then with isotonic saline solution.

EXAMPLE 1

1.5 mg. of thiomalic acid was dissolved in 1 ml. of pertechnetate solution, 1 drop of cupric sulphate solution (containing 11 micrograms of cupric ion) added, and the pH of the mixture adjusted to 4.0 with sodium bicarbonate. A 0.5 cm$^2$ piece of tin foil was added, and the mixture allowed to stand for 15 minutes. Analysis showed complete reduction of the pertechnetate with 97% complex formation.

EXAMPLE 2

2 mg. of N-acetyl-L-cysteine was dissolved in 1 ml. of pertechnetate solution. 1 drop of cupric sulphate solution (containing 11 micrograms of cupric ion) were added and the pH was adjusted to 3.0 with sodium bicarbonate. A 0.5 cm$^2$ piece of tin foil was added and the mixture allowed to stand for 15 minutes. Analysis showed complete reduction of the pertechnetate and 97% complex formation.

EXAMPLE 3

0.5 mg. of arsenazo was dissolved in 1 ml. of pertechnetate solution. 1 drop of cupric sulphate solution (containing 11 micrograms of cupric ion) was added and the pH adjusted to 4.0 with sulphuric acid. A 0.5 cm$^2$ piece of tin foil was added and the mixture allowed to stand for 30 minutes. Analysis showed a residue of 4% pertechnetate, and 84% complex formation.

EXAMPLE 4

6.4 mg. of sodium gluconate was dissolved in 1 ml. of pertechnetate solution, and 1 drop of copper sulphate solution (containing 378 micrograms of cupric ion) added. A piece of tin foil was added and the mixture allowed to stand for 15 minutes. Analysis showed complete reduction of pertechnetate and 97% complex formation.

In a repeat experiment, analysis showed complete reduction of pertechnetate and 98% complex formation.

Two control experiments performed without the copper sulphate addition gave rise to 7% and 8% complex formation.

EXAMPLE 5

The experiment of Example 4 was repeated using a more dilute copper sulphate solution, so that the drop contained only 50 micrograms of cupric ion. Analysis of duplicate experiments showed 97% and 98% complex formation. Two control experiments performed under identical conditions but without the copper sulphate showed 54% and 18% complex formation.

The experiment was again repeated but using still more dilute copper sulphate solution, so that the drop contained only 11 micrograms of cupric ion. Analysis of duplicate experiments again showed 97% and 98% complex formation, but this time pertechnetate ion was detectable in both preparations.

EXAMPLE 6

This Example shows performance of the method of this invention without a complexant.

1 Drop of copper sulphate solution (containing 50 micrograms of cupric ion) was mixed with 0.5 ml. of pertechnetate solution and a piece of tin foil added. After 15 minutes, the solution was removed and analysed. The tin foil was rinsed and the residual activity deposited upon it measured. The solution contained no pertechnetate, but only activity which behaved as technetium dioxide. The tin foil retained 4.5% of the total activity.

A duplicate experiment gave the same result, except that the residual activity associated with the tin foil was only 2.4%.

In a further experiment one drop of copper sulphate solution containing 11 micrograms of cupric ion was mixed with 2 ml. of pertechnetate solution and a piece of tin foil added. After 15 minutes the solution was analysed; no pertechnetate was present, only activity which behaved as technetium dioxide. This solution was injected intravenously into rats when there was rapid uptake in the liver and spleen. Dissection after two hours indicated that 95% of the activity was in the liver.

EXAMPLE 7

2 Vials were prepared, each containing 19.3 mg. of sodium gluconate and 11 micrograms of cupric ion as copper sulphate. The vial contents were dried by vacuum evaporation. A piece of tin foil was added to each vial. 1 Vial was capped in air, the other was evacuated, filled with nitrogen and then capped. The vials were allowed to stand for three days, then 3 ml. of pertechnetate solution was added to each. After 15 minutes, each vial was sampled for analysis. Both samples showed complete reduction of pertechnetate coupled with complex formation. Thereafter, the contents of each vial were analysed for copper and tin concentrations in solution. Analyses performed after 15 minutes, 1 hour, 2 hours, 4 hours and 6 hours all showed 1 to 2 parts per million of copper and 2 to 3 parts per million of tin in aqueous solution.

EXAMPLE 8

3×300 vial batches were prepared, each vial containing a freeze-dried mixture of 15 mg calcium gluconate and 15 $\mu$g of $Cu^{2+}$ as copper sulphate. To each vial of batch 1 was added a flexible strip of cellulose acetate supporting a piece of tin metal foil approx. 5×20 mm. To each vial of batch 2 was added a drop shaped pellet of tin metal weighing approx. 150 mg. To each vial of batch 3 was added either a 6 mm diam. tin foil disc or a piece of tinned copper wire about 2 mm diam. × 10 mm.

Vials from each batch were tested by adding 5 ml of Tc-99m generator eluate to reconstitute the freeze-dried components and allowing the active solution to stand in contact with the tin metal reductant for at least 15 minutes. Samples of the solution were analysed by thin layer chromatography to measure the extent of Tc-99m labelled gluconate complex formation and by intravenous injection into rats to assess biodistribution.

Over a period of more than 2 months all 25 vials tested showed reproducibly high complex formation (>95%) and identical animal biodistribution irrespective of the physical form of the tin metal reductant. Analysis of the solutions for $Sn^{2+}$ and $Cu^{2+}$ by atomic adsorbtion spectroscopy showed that $Sn^{2+}$ levels increased from about 1 ppm at 15 minutes to about 10 ppm at 8 hours and to >30 ppm at 48-170 hours after addition of generator eluate whilst the $Cu^{2+}$ levels remained almost constant at 2-3 ppm.

EXAMPLE 9

1 ml aliquots of solutions $1.2 \times 10^{-2}$ M in methylene diphosphonic acid, citric acid, sodium gluconate or EDTA and at least 10 $\mu$g $Cu^{2+}$ showed reproducibly good labelling (>90%) after addition of 2.5 ml of Tc-99m generator eluate and a piece of tin metal foil of at least 0.2 $cm^2$ surface area. Labelling of methylene diphosphonic acid and citric acid was more complete than for gluconate or EDTA for any given surface area of tin foil.

Sub-dispensed aliquots of the labelled complex solutions were stable for at least 1 hour after separation from the tin metal reductant although the gluconate complex showed signs of decomposition beyond this period.

I claim:

1. A method of reducing pertechnetate $TcO_4^-$, which method consists essentially of:
   (a) providing a vessel containing under sterile conditions tin or a tin-containing alloy as a reducing agent for the pertechnetate and a soluble salt of copper as an activator for the tin metal reducing agent,
   (b) aseptically introducing into the vessel an aliquot of a solution of pertechnetate,
   (c) and aseptically withdrawing from the vessel at least part of said aliquot comprising the reduced technetium.

2. A method as claimed in claim 1, wherein there is included in the vessel a complexant for the reduced technetium, or a colloid stabiliser.

3. A method as claimed in claim 1 or claim 2, wherein there is used from 0.5 to 50 ml of the aqueous solution of pertechnetate, from 0.1 to 10 $cm^2$ of tin or tin alloy, from 1 $\mu$g to 10 mg of the activator for the tin, and from 1 mg to 1 g of the complexant or colloid stabiliser.

4. A method as claimed in claim 1, wherein the pH of the mixture is from 3 to 7.

5. A closed container for producing, on introduction of a solution of technetium-99m as pertechnetate, technetium in a form suitable for diagnostic scanning, containing under sterile conditions tin or a tin-containing alloy as a reducing agent for the pertechnetate and a soluble salt of copper as an activator for the tin reducing agent.

6. A container as claimed in claim 5 wherein there is also present at least one of a complexant for the reduced technetium, a colloid stabiliser, and a buffer to keep the pH of the liquid mixture formed by introduction of the pertechnetate solution at a desired level.

7. A container as claimed in claim 5, wherein the contents are present in a freeze-dried state.

8. A container as claimed in claim 5, wherein the tin or tin alloy is fixed to a piece of flexible chemically inert foil, which flexible foil is positioned in curved configuration round the inside wall of the container.

* * * * *